United States Patent [19]

Noack et al.

[11] Patent Number: 5,306,913
[45] Date of Patent: Apr. 26, 1994

[54] METHOD AND APPARATUS FOR REMOTE OPTICAL DETECTION OF A GAS PRESENT IN AN OBSERVED VOLUME

[75] Inventors: Jean-Claude Noack, Cabries; Yves Guern, Jouques; Gérard Pelous, Aix en Provence, all of France

[73] Assignee: Bertin & Cie, Plaisir, France

[21] Appl. No.: 985,640

[22] Filed: Dec. 3, 1992

[30] Foreign Application Priority Data

Dec. 4, 1991 [EP] European Pat. Off. ........ 91403281.8

[51] Int. Cl.⁵ .............................................. G01N 21/35
[52] U.S. Cl. .................................. 250/338.5; 250/330
[58] Field of Search ............................. 250/338.5, 330

[56] References Cited

U.S. PATENT DOCUMENTS

| | | | |
|---|---|---|---|
| 4,390,785 | 6/1983 | Faulhaber et al. | 250/330 |
| 4,725,733 | 2/1988 | Horman et al. | 250/339 |
| 5,001,346 | 3/1991 | Barkhoudarian | 250/330 |
| 5,026,992 | 6/1991 | Wong | 250/343 |

FOREIGN PATENT DOCUMENTS

| | | |
|---|---|---|
| 348141 | 12/1989 | European Pat. Off. |
| 2176889 | 1/1987 | United Kingdom |

OTHER PUBLICATIONS

H. S. Lee, H. H. Zwick and S. M. Till, "Gas filter correlation instrument for the remote sensing of gas leaks." *Rev. Sci. Instrum.*, vol. 56, No. 9 (Sep. 1985) pp. 1812-1819.

W. D. Hesketh, H. G. Reichle, W. A. Massey, T. V. Ward and H. H. Zwick, "A Gas Filter Coorelation Instrument for Atmospheric Trace Constituent Monitoring." Presented at the *Fifth Annual Remote Sensing of Earth Resources Conference*, Tullahoma, Tenn. (Mar. 29-31, 1976) L-10720.

L. L. Acton, M. Griggs, G. D. Hall, C. B. Ludwig, W. Malkmus, W. D. Hesketh anbd H. Reichle, "Remote Measurement of Carbon Monoxide by a Gas Filter Correlation Instrument." *AIAA Journal*, vol. 11, No. 7 (Jul. 1973) pp. 899-900.

X. Maldague et al., "Dual Imager and its Applications to Active Vision Robot Welding, Surface Inspection, and Two-Color Pyrometry", *Optical Engineering*, vol. 28, No. 8, Aug. 1989, pp. 872-880.

Primary Examiner—Constantine Hannaher
Attorney, Agent, or Firm—Bell, Seltzer, Park & Gibson

[57] ABSTRACT

A method and apparatus for remote optical detection of a gas present in an observed volume using a thermal imager or camera including one or more sensitive elements which are sensitive to radiant fluxes in a determined band of wavelengths, two filters interposable on the optical axis of the camera, the filters having similar transmission bands, one of which includes an absorption line characteristic of the looked-for gas, while the other of which is complementary to said absorption line, and signal processing means for taking the difference between the radiated fluxes received from two points at different temperatures in the volume as observed first through one of the filters and then through the other filter, for taking the ratio of said differences, and for deducing therefrom whether the gas is present in the observed volume.

13 Claims, 2 Drawing Sheets

METHOD AND APPARATUS FOR REMOTE OPTICAL DETECTION OF A GAS PRESENT IN AN OBSERVED VOLUME

The invention relates to a method and apparatus for remote optical detection of a gas, e.g. a polluting gas, present in an observed volume.

BACKGROUND OF THE INVENTION

It is known that gases are characterized in particular by molecular or atomic absorption lines at wavelengths that are determined very accurately and that it is possible to detect the presence of a gas in the atmosphere by identifying one or more absorption lines.

A "lidar" type system can be used for this purpose, the system comprising a laser emitting pulses towards the observed volume at a wavelength which corresponds to an absorption line of the looked-for gas. The signals backscattered by the atmosphere are detected, and the presence or absence of the gas in the atmosphere is deduced therefrom.

That known system suffers from certain drawbacks, including relatively high cost, weight, and bulk, with uses thereof being limited to the wavelengths of the laser pulses, and with the dangers associated with emitting high-energy pulses (danger for the eye, risk of explosion in certain environments, e.g. of petroleum gas or of chemical gas).

Proposals have also been made to detect the presence of a gas in the atmosphere by radiometric or spectroscopic techniques, enabling a spectral distribution of energy received or transmitted over a band of wavelengths to be obtained, with such techniques being based on the fact that a gas which absorbs energy at a certain wavelength also re-emits energy at said wavelength. However, the sensitivity of such techniques is highly variable. To obtain high sensitivity, it is necessary to control the spectral emittance of the source and to dispose the emitter and the receiver on opposite sides of the observed volume, or else when the emitter and the receiver are on the same side of the observed volume, to dispose a reflector on the other side of said volume, thereby requiring two points of access to said volume, and also fixing the measurement optical path. In other cases where the characteristics of the emitter, and in particular its temperature, are not under control, the results obtained depend on the difference between the temperature of the gas and the background temperature, i.e. the temperature to be found behind the gas and which serves as an emitter, with sensitivity being zero when said difference is zero.

Patent GB 2 176 889 proposes a system for detecting a gas in a volume to be monitored, on the basis of the ratio of the radiant fluxes from said volume in two wavelength bands. One of which corresponds substantially to an absorption line of the gas and the other of which essentially comprises wavelengths in which the gas does not have an absorption peak. A drawback of that system is that it operates only if the gas to be detected is considerably colder than its environment.

An object of the invention is to provide a method and apparatus for passive detection of a gas present in an observed volume, but without being subjected to the above drawbacks.

Another object of the invention is to provide a method and apparatus of this type enabling a gas present in an observed volume to be detected remotely from a single point of access to said volume.

Another object of the invention is to provide a method and apparatus of this type enabling a gas present in an observed volume to be detected quickly in real time.

Another object of the invention is to provide a method and apparatus of this type enabling the atmospheric environment of an area such as an industrial site, e.g. an oil refinery or a chemical factory, to be monitored remotely.

SUMMARY OF THE INVENTION

To this end, the invention provides a method for remote optical detection of a gas, e.g. a polluting gas, present in an observed volume, the method consisting in:
   detecting the radiant fluxes coming from at least two different temperature points of said volume, said fluxes passing through the looked-for gas and being detected through a first filter having a transmission band that includes an absorption line characteristic of the looked-for gas;
   taking the difference between the fluxes detected through the first filter;
   detecting the radiant fluxes coming from the abovespecified two points through a second filter having a transmission band similar to that of the first filter and complementary to said absorption line of the looked-for gas:
   taking the difference between the fluxes detected through the second filter;
   taking the ratio of the above-specified differences; and
   deducing possible presence of the gas in the observed volume from the value of said ratio.

The fluxes detected in this way through the filter whose transmission band does not include the absorption line characteristic of the looked-for gas have values that are not changed by the presence or the absence of the looked-for gas in the observed volume, whereas the fluxes detected through the other filter have values that depend on the presence of the looked-for gas, and on its concentration.

The ratio of these fluxes is thus a function of the concentration of the looked-for gas and has the advantage of being substantially independent, to a first approximation, of temperature and also of transmission through the optical system of the detection device.

Furthermore, the difference between the fluxes detected through a single filter and coming from two points at different temperatures in the observed volume can be used to eliminate emission specific to the looked-for gas (which emission considerably degrades the sensitivity of the above-mentioned radiometric techniques), and a result is obtained from the ratio of these differences which is independent of the temperatures of the two points and of the difference between said temperatures.

This processing can be generalized to a set of points or areas distributed in predetermined manner within the observed volume so as to obtain a map of gas concentration in the observed volume.

Advantageously, the method of the invention consists in using a thermal imager or camera for detecting the abovementioned fluxes, and in processing the electrical signals provided by the thermal imager or camera in the above-mentioned manner, which signals correspond to the above-mentioned fluxes.

These signals may be digitized and applied to a data processing system which obtains local or geographic averages and time averages of the signals by integration, thereby reducing noise and increasing measurement accuracy.

The method of the invention may be used for detecting two different gases in the observed volume, in which case it consists in using two filters having transmission bands that are similar in wavelength, with the transmission band of one of the filters being complementary to an absorption line of one of the two gases and the transmission band of the other filter being complementary to an absorption line of the other one of the gases, and in deducing the presence of one or the other gas in the observed volume on the basis of the value of the ratio of the fluxes detected through the two filters.

When the value of the ratio of the fluxes increases, then the presence of one of the two looked-for gases is detected, and when the value of the ratio decreases, then the presence of the other gas is detected.

In a variant, it is possible to use two filters, one of which has a transmission band comprising the absorption lines of both looked-for gases, and the other of which has a transmission band which is complementary to said absorption lines, with the presence of one or other of the gases being deduced from the value of the ratio of the fluxes detected through the two filters.

The invention also provides apparatus for remote optical detection of a gas in an observed volume, the apparatus comprising:
  a thermal imager or camera including at least one sensitive element sensitive to radiant fluxes in a determined band of wavelengths, and an optical system enabling an image of at least a portion of the observed volume to be formed on said sensitive element;
  at least two filters suitable for being interposed on the optical axis of the thermal imager or camera for detecting the radiant fluxes of the observed volume through each of the filters, said filters having similar transmission bands in the above-mentioned band of wavelengths, the band of one of the filters including at least one absorption line of the looked-for gas and the band of the other filter being complementary to said absorption line; and
  signal processing means comprising means for selecting the signals provided by said sensitive element and corresponding to the fluxes from at least two points at different temperatures in the observed volume the fluxes from these two points being detected through the looked-for gas, means for establishing the differences between the fluxes from these two points as detected through one and then the other one of the filters, and means for taking the ratio of these differences.

This apparatus may also comprise means for comparing fluxes from adjacent areas in the observed volume, for obtaining the differences between said fluxes as detected through one of the filters and the differences between these fluxes as detected through the other filter, means for establishing the ratios between said differences, and means for comparing said ratios to establish a map of the concentration of the gas in the observed volume.

In general, the transmission bands of the above-mentioned filters are of widths in wavelength that are so determined that the fluxes received by the thermal imager or camera correspond to a linear response region of the thermal imager or camera.

This avoids working under conditions in which the levels of the received fluxes are too low or too high (saturation of the sensitive component(s)).

BRIEF DESCRIPTION OF THE DRAWINGS

The invention will be better understood and other characteristics, details, and advantages thereof will appear more clearly on reading the following description given by way of example and made with reference to the accompanying drawings, in which.

MORE DETAILED DESCRIPTION

Figure 1:
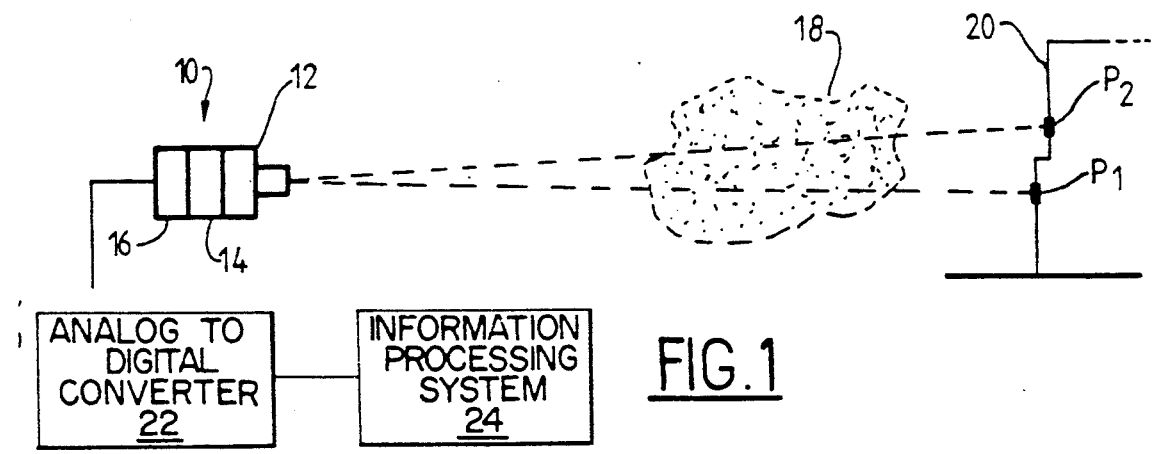
FIG. 1 is a highly diagrammatic representation of gas detection apparatus of the invention.

Reference is made initially to FIG. 1 in which detection apparatus of the invention is shown diagrammatically together with its conditions of use.

The apparatus comprises a thermal imager or camera 10 essentially comprising an optical system 12, a filter 14, and at least one sensitive element 16 on which the optical system 12 forms, via the filter 14, an image of an observed volume, which volume may, for example, include a cloud 18 of a lookedfor gas together with a background 20.

When working in the visible spectrum, the camera may be a television camera or the like, for example, or it may be a thermographic camera, i.e. an instrument capable of providing direct temperature measurements on its line of sight. The term "thermal imager" is used herein as a general term to designate any instrument capable of providing an image of the temperature of a volume it is looking at, i.e. an image whose color or gray scale density varies as a function of the temperature of its point of aim.

Depending on circumstances, and as a function of the wavelengths at which measurements or detections are performed, the thermal imager or camera may comprise a single sensitive element which is associated with a system of scanning mirrors, or else it may comprise a group or matrix of sensitive elements, optionally enabling the system of scanning mirrors to be omitted.

In the apparatus shown in FIG. 1, the output signals from the sensitive element(s) 16 are applied via an analog-to-digital converter 22 to an information processing system 24 such as a programmed microcomputer.

The apparatus of the invention in fact includes two filters 14 which are superposed or which are interposed sequentially in turn on the optical axis of the thermal imager or camera, e.g. by means of a motorized system.

The two filters have wavelength transmission bands that coincide to a large extent and which are preferably similar overall, but one of them includes an absorption line of the gas to be detected while the other one is substantially complementary to said absorption line.

This concept is explained in greater detail with reference to FIGS. 2 to 4.

Figure 2:
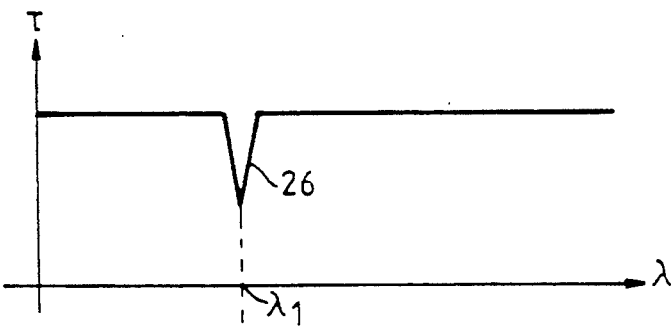
FIG. 2 is a diagrammatic graph showing the appearance of an absorption line of the gas.

FIG. 2 is a diagram showing how transmission $\tau$ through a gas to be detected varies over a certain band of wavelengths $\lambda$, with the transmission curve having an absorption line 26 at a wavelength $\lambda 1$, and with the amplitude of the absorption line being a function of the concentration of the gas, and the width of the absorption line, may be, for example, in the order of a few tens or hundreds of nm.

Figure 3:
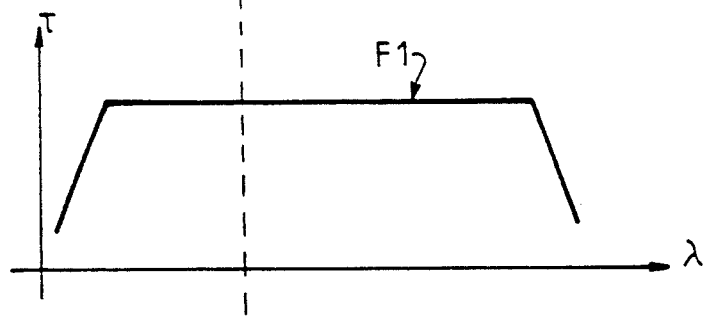
FIGS. 3 and 4 are diagrams showing the transmission bands of two filters as a function of wavelength.
Figure 4:
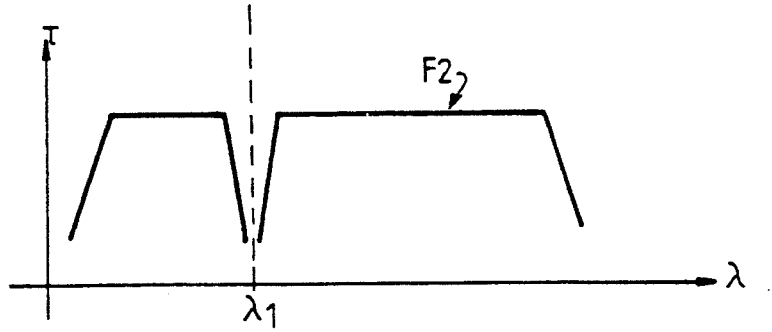

FIG. 3 is a diagram of the transmission curve as a function of wavelength of one of the two filters used in the invention, e.g. a first filter which is referred to below by the reference F1. This transmission band includes the wavelength $\lambda 1$ of the absorption line of the gas to be detected, and it extends over a band of wavelengths that is greater than the width of the absorption line 26 of the gas to be detected.

The other filter used in the invention, referred to below by the reference F2, has a transmission band with the appearance shown in FIG. 4, which band does not include the wavelength $\lambda 1$ of the absorption line 26 of the gas to be detected and is, so to speak, complementary to said absorption line relative to the transmission band of the filter F1 as shown in FIG. 3.

Thus, when the filter F1 is placed on the optical axis of the thermal imager or camera 10, the radiant flux received by the sensitive element is a function of the presence or the absence of a cloud 18 of gas to be detected in the observed volume, and is also a function of the concentration of said gas.

In contrast, when the filter F2 is placed on the optical axis of the thermal imager or camera 10, the flux that it transmits to the sensitive element is independent of the presence or absence of a cloud 18 of gas to be detected in the observed volume.

The ratio of the fluxes provided sequentially to the sensitive element via the filter F1 and then via the filter F2 provides a magnitude which is a function of the concentration of the gas to be detected in the observed volume but which is independent of temperature and of the transmission characteristics of the optical system.

In a variant, the filter F1 may be placed on the optical axis and measurements may be performed, after which the filter F2 is placed on the optical axis while leaving the filter F1 in place, with measurement being performed again.

In addition, when the fluxes provided by two points or areas P1 or P2 having different temperatures in the observed volume are detected sequentially through the filters F1 and F2, said two points or areas being seen by the thermal imager or camera 10 through the cloud 18 of gas to be detected, it is possible to eliminate the effect of emission by the cloud of gas 18 by taking the difference between the fluxes from the points P1 and P2 as seen through the filter F1 and then through the filter F2, and subsequently taking the ratio between these differences.

The fluxes from the points P1 and P2 transmitted through the cloud of gas 18 towards the thermal imager or camera can be written as follows:

$$\phi_1 = \phi_{p1} \times \tau_g + \phi_g$$

$$\phi_2 = \phi_{p2} \times \tau_g + \phi_g$$

where:

$\phi_{p1}$ = flux emitted by point P1 at temperature T1;
$\phi_{p2}$ = flux emitted by point P2 at temperature T2;
$\tau_g$ = transmission of the cloud of gas 18; and
$\tau_g$ = flux emitted by the cloud of gas at temperature $T_g$.

The difference $\delta$ between the fluxes $\phi_1$ and $\phi_2$ is thus independent of the flux emitted by the cloud of gas 18:

$$\delta = \phi_1 - \phi_2 = (\phi_{p1} - \phi_{p2}) \times \tau_g$$

Let D1 be the difference between the output signals from the sensitive element 16 corresponding to fluxes $\phi_1$ and $\phi_2$ as received through the filter F1, and let D2 be the difference between these output signals corresponding to fluxes $\phi_1$ and $\phi_2$ as received through the filter F2.

These differences D1 and D2 can be approximated by the following equation3:

$$D1 = G \times (\delta\lambda_1 - \delta\lambda_g(1 - \tau_g))\sigma(T_1^4 - T_2^4)$$

$$D2 = G \times \delta\lambda_2 \times \sigma(T_1^4 - T_2^4)$$

where:
G = overall gain of the thermal imager or camera;
$\delta\lambda_1$ = the width of the transmission band of filter F1 in wavelength;
$\delta\lambda_2$ = the width of the transmission band of filter F2 in wavelength;
$\delta\lambda_g$ = the half width of the absorption line of the gas to be detected, in wavelength; and
$\sigma$ = Stefan's constant.

It can be seen that the ratio D1/D2 is independent of the overall gain of the thermal imager or camera, of the temperature difference between the points P1 and P2, of the temperatures of these two points, and of the temperature of the gas to be detected.

Further, when a television camera is used for detecting gases in the visible region, the camera generally comprises three matrices of sensitive elements (one per primary color), each of which is associated with a color filter. These color filters may be replaced by filters in accordance with the invention, thereby making it possible to omit a motorized system for displacing filters, and also making it possible to perform simultaneous detection on fluxes passing through different filters.

In other cases also, it is likewise possible to detect these fluxes simultaneously by using two sensitive elements or groups of sensitive elements in parallel, with each sensitive element or group of sensitive elements being associated with one of the above-mentioned filters.

To reduce detection noise and to increase measurement accuracy, the invention also provides for using the data processing system 24 to determine local or geographic averages on the signals provided by the sensitive element(s) 16 and corresponding to fluxes received from points in the immediate vicinity of the points P1 and P2 respectively, or from points lying in the areas P1 and P2, and also to determine time averages of these signals over a predetermined period of time.

The invention also provides for splitting up the observed volume into measurement areas, for detecting the fluxes emitted by a plurality of points in each area via a first filter, and for obtaining an average of the fluxes detected in such an area, for comparing the average for one area with the averages for adjacent areas, and for obtaining the differences between said averages for the set of areas in the observed volume, for likewise performing the same operations with the second filter to obtain other differences between averages for the set of measurement areas, for taking the ratios between the differences between the averages obtained using the first filter and the differences between the averages obtained using the second filter, and for deducing a map of gas concentration in the observed volume from the values of these ratios. Before taking a ratio, a check is made to ensure that the abovementioned differences are not zero.

In another aspect of the invention, it is advantageous for the filters F1 and F2 to have transmission bands that are relatively wide (e.g. a few microns wide) compared with the absorption line 26 of the gas to be detected, thereby ensuring that the flux levels received by the thermal imager or camera 10 correspond to a region of substantially linear response in the sensitive element(s) 16.

In addition, these relatively wide transmission band filters of the invention emit relatively little and may be used without cooling, thus constituting a major practical advantage compared with the narrow band filters that are conventionally used in radiometric and spectroscopic techniques.

Figure 5:
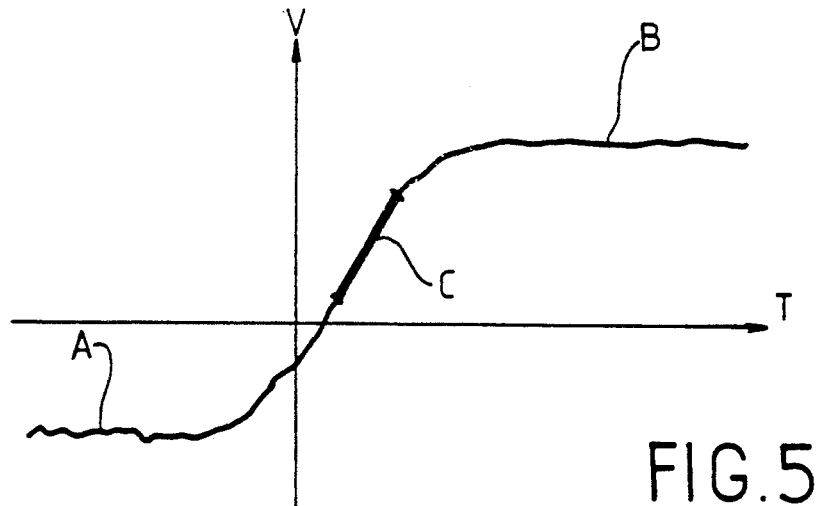
FIG. 5 is a diagrammatic graph showing how the output signal from a thermal imager or camera varies as a function of temperature.

As an illustration, FIG. 5 shows how the output signal (in volts) from a sensitive element 16 varies as a function of temperature. Operating points corresponding to portions A and B of the curve must be avoided, and the widths of the transmission bands of the filters F1 and F2 are designed so as to lie on portion C of the curve.

Figure 6:
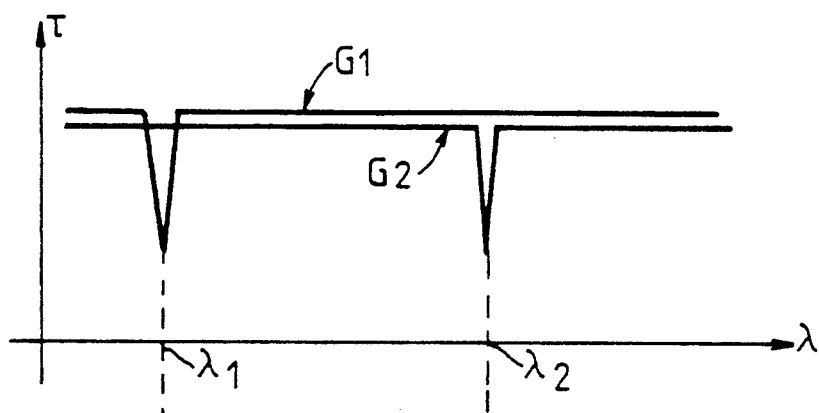
FIG. 6 is a graph showing the absorption lines of two looked-for gases.
Figure 7:
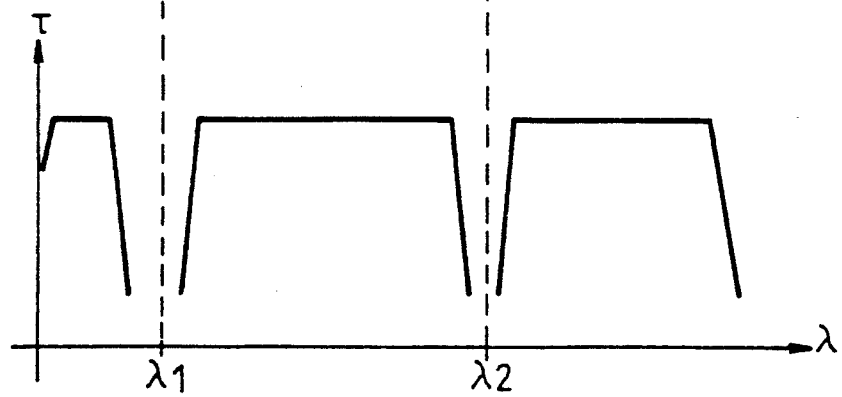
FIG. 7 is a graph showing the transmission band of a filter suitable for use in detecting both of these gases.

When it is desired to detect the presence of two different gases in the atmosphere, one of which, G1, has an absorption line at wavelengths λ1 and the other of which, G2, has an absorption line at wavelength λ2, as shown diagrammatically in FIG. 6, it is possible for this purpose to use a filter whose transmission band includes both wavelengths λ1 and λ2, together with a filter whose transmission band is complementary to the absorption lines at the wavelengths λ1 and λ2 as shown diagrammatically in FIG. 7. Under such circumstances, the presence of one and/or the other gas in the absorbed volume can be deduced from the value of the ratio D1/D2 without it being possible to identify which of the two gases is present in said volume.

It is also possible to use two filters, one of which has a transmission band complementary to the absorption line of the gas G1 at wavelength λ1, while the other has a transmission band complementary to the absorption line of the gas G2 at wavelength λ2. Under such circumstances, the value of the ratio D1/D2 makes it possible to identify which of the two gases is present in the observed volume, with the value of this ratio increasing in the presence of one of the gases and decreasing in the presence of the other gas.

For detecting a plurality of different gases in the observed volume, it is also possible to use filters, each having a transmission band which is complementary to an absorption line that is characteristic of a gas to be detected. Under such circumstances, fluxes detected sequentially through the filters must be compared in pairs and the values of the ratios Di/Dj serve to identify the gas(es) detected in the observed volume.

It will be observed that a thermal imager or camera is generally already fitted with a filter which, under certain conditions, is more or less equivalent to the filter F1 that includes the absorption line of the gas to be detected. Under such circumstances, it therefore suffices to use a single filter F2 and to perform measurements when said filter lies on the optical axis of the thermal imager or camera and when it lies off the axis. Such a variant does not thereby fall outside the scope of the invention.

We claim:

1. A method for remote optical detection of a gas, e.g. a polluting gas, present in an observed volume, the method comprising:
   detecting the radiant fluxes coming from at least two different temperature points of said volume, said fluxes passing through the looked-for gas and being detected through a first filter having a transmission band that includes an absorption line characteristic of the looked-for gas;
   taking the difference between the fluxes detected through the first filter;
   detecting the radiant fluxes coming from the above-specified two points through a second filter having a transmission band similar to that of the first filter and complementary to said absorption line of the looked-for gas;
   taking the difference between the fluxes detected through the second filter;
   taking the ratio of the above-specified differences; and
   deducing possible presence of the gas in the observed volume from the value of said ratio.

2. A method according to claim 1, further comprising detecting the above-mentioned fluxes through one of the filters F1, and then through both filters F1, F2 while they are superposed.

3. A method according to claim 1, further comprising using a thermal imager or camera for detecting the above-mentioned fluxes, and processing the electrical signals provided by the thermal imager or camera in the above-mentioned manner, which signals correspond to the above-mentioned fluxes.

4. A method according to claim 3, further comprising: digitizing the signals provided by the thermal imager or camera; applying the digitized signals to a data processing center; and using said system to obtain time averages and local or geographic averages on said signals by integration in order to reduce noise and increase measurement accuracy.

5. A method according to claim 1, further comprising: detecting fluxes from areas that are distributed in predetermined manner within the observed volume through one filter and then through the other filter; comparing the flux from an area with the fluxes from adjacent areas to obtain first differences between the fluxes detected through one of the filters and second differences between the fluxes detected through the other filter and deducing a map of gas concentration in the observed volume from the ratios between the first differences and the second differences.

6. A method according to claim 1, in which, in order to detect two different gases in the observed volume, the method comprises using two filters having similar transmission bands, the band of one of the filters being complementary to an absorption line characteristic of one of the two gases, and the band of the other filter being complementary to an absorption line characteristic of the other one of the gases, the method further comprising deducing the presence of one or other of the gases in the observed volume from the value of the ratio of the fluxes detected through each of the two filters.

7. A method according to claim 1, in which, in order to detect two different gases in the observed volume, the method further comprising using two filters having similar transmission bands, the band of one of the filters including an absorption line characteristic of one of the two gases and another absorption line characteristic of the other gas, the transmission band of the other filter being complementary to said absorption lines, and in deducing in presence of one or other of the gases in the observed volume on the basis of the value of the ratio of the fluxes detected through each of the two filters.

8. Apparatus for remote optical detection of a gas, in an observed volume, e.g. a polluting gas, the apparatus comprising:
   a thermal imager or camera including at least one sensitive element sensitive to radiant fluxes in a determined band of wavelengths, and an optical system enabling an image of at least a portion of the observed volume to be formed on said sensitive element;
   at least two filters suitable for being interposed on the optical axis of the thermal imager or camera for detecting the radiant fluxes of the observed volume through each of the filters, said filters having similar transmission bands in the above-mentioned band of wavelengths, the band of one of the filters including at least one absorption line of the looked-for gas and the band of the other filter being complementary to said absorption line; and
   signal processing means comprising means for selecting the signals provided by said sensitive element and corresponding to the fluxes from at least two points at different temperatures in the observed volume, the fluxes from these two points being detected through the looked-for gas, means for establishing the differences between the fluxes from these two points as detected through one and then the other one of the filters and means for taking the ratio of these differences.

9. Apparatus according to claim 8, comprising means for comparing fluxes from adjacent areas in the observed volume, for obtaining the differences between said fluxes as detected through one of the filters and the differences between these fluxes as detected through the other filter, means for establishing the ratios between said differences, and means for comparing said ratios to establish a map of the concentration of the gas in the observed volume.

10. Apparatus according to claim 8, comprising means for digitizing the signals provided by the sensitive element.

11. Apparatus according to claim 8, in which, to detect a second gas present in the observed volume and characterized by another absorption line in the above-mentioned band of wavelengths, the transmission bands of the two above-mentioned filters are respectively complementary to the absorption line of the first line and to the absorption line of the second gas.

12. Apparatus according to claim 8, in which, to detect other gases present in the observed volume and characterized by other absorption lines in the above-specified band of wavelengths, the transmission bands of the two above-mentioned filters are determined so that one of them includes the absorption lines of the looked-for gases while the other one is complementary to said absorption lines.

13. Apparatus according to claim 8, in which the transmission bands of the above-mentioned filters are of widths in wavelength that are so determined that the fluxes received by the thermal imager or camera correspond to a linear response region of the thermal imager or camera.

* * * * *

UNITED STATES PATENT AND TRADEMARK OFFICE
CERTIFICATE OF CORRECTION

PATENT NO. : 5,306,913
DATED : April 26, 1994
INVENTOR(S) : Noack et al.

It is certified that error appears in the above-identified patent and that said Letters Patent is hereby corrected as shown below:

Column 1, line 17, delete "a".

Column 1, line 57, ". One" should be -- , one --.

Column 3, line 52, after "volume" insert -- , --.

Column 4, line 37, "lookedfor" should be -- looked-for --.

Column 6, line 4, "Tg" should be -- $\phi g$ --.

Column 7, line 11, "abovementioned" should be -- above-mentioned --.

Column 9, line 10, delete "in".

Column 9, line 11, "in" (first occurrence) should be -- the --.

Signed and Sealed this

Sixth Day of September, 1994

Attest:

BRUCE LEHMAN

*Attesting Officer*  *Commissioner of Patents and Trademarks*